(12) United States Patent
Park et al.

(10) Patent No.: US 10,092,177 B1
(45) Date of Patent: Oct. 9, 2018

(54) DEVICE, SYSTEM AND METHOD FOR IMAGE DISPLAY WITH A PROGRAMMABLE PHASE MAP

(71) Applicant: Verily Life Sciences LLC, Mountain View, CA (US)

(72) Inventors: Sohyun Park, Sunnyvale, CA (US); Igor Landau, Boulder, CO (US)

(73) Assignee: Verily Life Sciences LLC, Mountain View, CA (US)

(*) Notice: Subject to any disclaimer, the term of this patent is extended or adjusted under 35 U.S.C. 154(b) by 0 days.

(21) Appl. No.: 14/985,305

(22) Filed: Dec. 30, 2015

(51) Int. Cl.
*A61B 3/10* (2006.01)

(52) U.S. Cl.
CPC .................. *A61B 3/1015* (2013.01)

(58) Field of Classification Search
CPC .. G02B 27/0172; G02B 27/01; G02B 27/017; G02B 27/0081; G02B 27/0093; G02B 27/0101; G02B 27/0103; G09F 19/18; G09G 3/003; G09G 3/02; A61B 3/101; A61B 3/1015; G02C 7/04; G02C 11/10
USPC .... 351/211, 158; 359/13, 32, 567, 630, 632; 345/88, 211
See application file for complete search history.

(56) References Cited

U.S. PATENT DOCUMENTS

| | | | |
|---|---|---|---|
| 8,446,341 B2 | 5/2013 | Amirparviz et al. | |
| 2006/0176449 A1 | 8/2006 | Azar et al. | |
| 2007/0236769 A1 | 10/2007 | Zalevsky | |
| 2010/0283774 A1* | 11/2010 | Bovet | G02B 27/017 345/211 |
| 2010/0296143 A1* | 11/2010 | Reichelt | G03H 1/02 359/32 |
| 2012/0008181 A1 | 1/2012 | Cable et al. | |
| 2012/0105310 A1* | 5/2012 | Sverdrup | G02B 27/017 345/8 |
| 2012/0199995 A1* | 8/2012 | Pugh | A61N 5/0618 264/1.36 |
| 2013/0222384 A1* | 8/2013 | Futterer | G02B 5/32 345/426 |
| 2013/0265622 A1* | 10/2013 | Christmas | G02B 27/0103 359/9 |

(Continued)

FOREIGN PATENT DOCUMENTS

| | | |
|---|---|---|
| WO | WO 2006012679 | 2/2006 |
| WO | WO 2013086078 | 6/2013 |

(Continued)

OTHER PUBLICATIONS

U.S. Appl. No. 14/724,095, filed May 28, 2015, Park et al.
U.S. Appl. No. 14/724,173, filed May 28, 2015, Park et al.

*Primary Examiner* — Mustak Choudhury
(74) *Attorney, Agent, or Firm* — Christensen O'Connor Johnson Kindness PLLC

(57) ABSTRACT

A near-eye display including a light source, an optical system, and a phase map including multiple pixels. The optical system is configured to receive illumination light from the light source and output the illumination light as an in-phase wavefront. Control logic of the near-eye display is coupled to variously program different phase patterns of the phase map at different times. The phase patterns are each to variously adjust phases of respective portions of the in-phase wavefront. For each of the phase patterns, the phase map is to form a different respective image in response to being illuminated by the in-phase wavefront.

22 Claims, 12 Drawing Sheets

(56) References Cited

U.S. PATENT DOCUMENTS

| | | |
|---|---|---|
| 2014/0002911 A1 | 1/2014 | Peloux et al. |
| 2014/0049451 A1 | 2/2014 | Sugiyama et al. |
| 2014/0118829 A1* | 5/2014 | Ma .................. G02B 5/1885 |
| | | 359/567 |
| 2014/0368812 A1 | 12/2014 | Humphrey et al. |
| 2015/0005604 A1* | 1/2015 | Biederman .......... G02C 7/04 |
| | | 600/347 |

FOREIGN PATENT DOCUMENTS

| | | |
|---|---|---|
| WO | WO 2014151877 | 9/2014 |
| WO | WO 2014155288 | 10/2014 |
| WO | WO 2015104239 | 7/2015 |

* cited by examiner

IMAGE 383

IMAGE 384

IMAGE 385

IMAGE 386

DEVICE, SYSTEM AND METHOD FOR IMAGE DISPLAY WITH A PROGRAMMABLE PHASE MAP

BACKGROUND

1. Technical Field

This disclosure relates generally to image display systems, and more particularly, but not exclusively to near-eye displays that utilize phase maps.

2. Background Art

Near-eye displays are wearable devices that form a display image in a wearer's field of view. Near-eye displays have numerous practical and leisure applications. Aerospace applications permit a pilot to see vital flight control information without taking their eye off the flight path. Public safety applications include tactical displays of maps and thermal imaging. Other application fields include video games, transportation, and telecommunications.

Since near-eye displays are wearables, improvements in power consumption and form factor are highly desirable. Conventional near-eye displays often include a micro-display and an image relay that includes lenses and/or mirrors to direct the images generated by the micro-display to the eye of a wearer of the near-eye display. These various optical components add bulk to the near-eye display. Furthermore, the optical components must be fabricated with very tight manufacturing tolerances and also be precisely aligned to maintain the fidelity of the image generated by the micro-display. The optical components must also be designed to maintain the colors of the image as the image light propagates through the image relay. Therefore, a near-eye display that reduces the bulk, power consumption, and optical fidelity requirements of existing near-eye displays is desirable.

BRIEF DESCRIPTION OF THE DRAWINGS

The various embodiments of the present invention are illustrated by way of example, and not by way of limitation, in the figures of the accompanying drawings and in which.

DETAILED DESCRIPTION

Embodiments of near-eye (e.g., including on-eye) displays that include phase maps and systems that include near-eye displays are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1A:
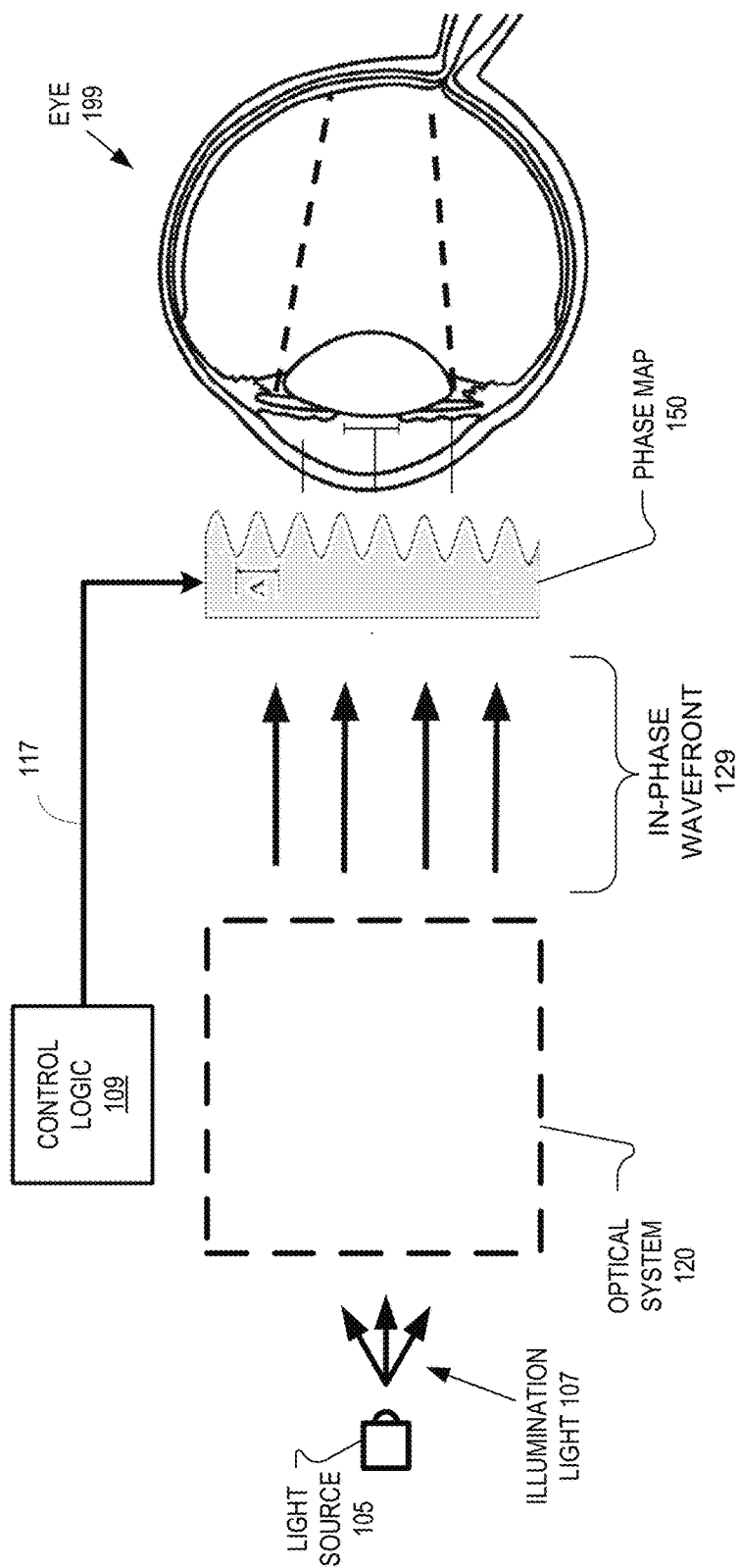
FIGS. 1A and 1B illustrate an example near-eye display that includes a programmable phase map, in accordance with an embodiment of the disclosure.

FIG. 1A illustrates an example near-eye display 100 that includes a phase map 150, in accordance with an embodiment of the disclosure. Near-eye display 100 includes a light source 105, optical system 120, and phase map 150. In one embodiment, light source 105 is a laser diode that emits visible narrow-band (e.g. 1-2 nm) light. In another embodiment, light source 105 is a light-emitting-diode ("LED") that emits broader spectrum (e.g. 50 nm band) colored light. The LEDs may be red, green, or blue, for example. In one embodiment, light source 105 is a monochromatic green LED.

Optical system 120 may include various optical components such as diffractive and refractive lenses, mirrors, filters, and collimators, depending on the specific requirements of the near-eye display. Optical system 120 is configured to receive illumination light 107 emitted by light source 105 and output the illumination light as in-phase (coherent) wavefront 129. Although in-phase wavefront 129 is coherent—and in some embodiments, may include a varying combination of coherent light and incoherent light—it may not necessarily be collimated. In other words, in-phase wavefront 129 may be diverging or converging, in some embodiments. In other embodiments, in-phase wavefront 129 may be both coherent and collimated. Optical system 120 is configured to illuminate phase map 150 with in-phase wavefront 129.

Phase map 150 is an optical element configured to variously adjust the phase of respective portions of in-phase wavefront 129. Such phase adjustment may facilitate formation of various images each at a retina-distance from phase map 150 when phase map 150 is illuminated by in-phase wavefront 129. Such images may be generated dynamically and may vary over time—e.g., based on signals variously provided to multiple pixels of phase map 150. For the purposes of the disclosure, retina-distance will be defined as the distance between the phase map and the retina of a human eye. In one embodiment, the retina distance is less than 30 mm which is less than the nearest focusing capability of the human eye.

By way of illustration and not limitation, control logic 109 of near-eye display 100 (or alternatively, coupled to near-eye display 100) may comprise circuitry configured to provide signals 117 to independently control some or all pixels of phase map 150. Such pixels may be variously configured each to receive a respective portion of in-phase wavefront 129 and a respective one or more of signals 117. Based on control signals 117, pixels may each adjust a phase of the respective wavefront portion received by that pixel. For a given image, signals 117 may provide a programming of the pixels with a corresponding phase pattern to variously diffract or scatter in-phase wavefront 129 as image light 173 to form a corresponding real image directly onto the retina of a human eye.

The phase adjustment by a given pixel of phase map 150 may change over time—e.g., across successive images to be displayed for eye 199. Alternatively or in addition, the phase adjustment by a given pixel may be different than (e.g., independent of) concurrent phase adjustment by another pixel of phase map 150. Control signals 117 may thus facilitate dynamic control of phase map 150 for the display over time of multiple images, such at those of an animation. Some or all such images may be displayed, for example, independent of phase map 150 being pre-recorded for the display of any one particular image. In one embodiment, light source 105 sequentially outputs light of different respective wavelengths (e.g., including a sequence of red light, green light, and blue light or a sequence of various other complementary colors), where for one such sequence, different wavelengths of light are to successively illuminate the same programmed phase pattern (or alternatively, different respective phase patterns) of phase map 150. In some embodiments, a phase pattern may provide for wavelength scaling to mitigate, or compensate for, diffractive chromatic dispersion.

Figure 1B:
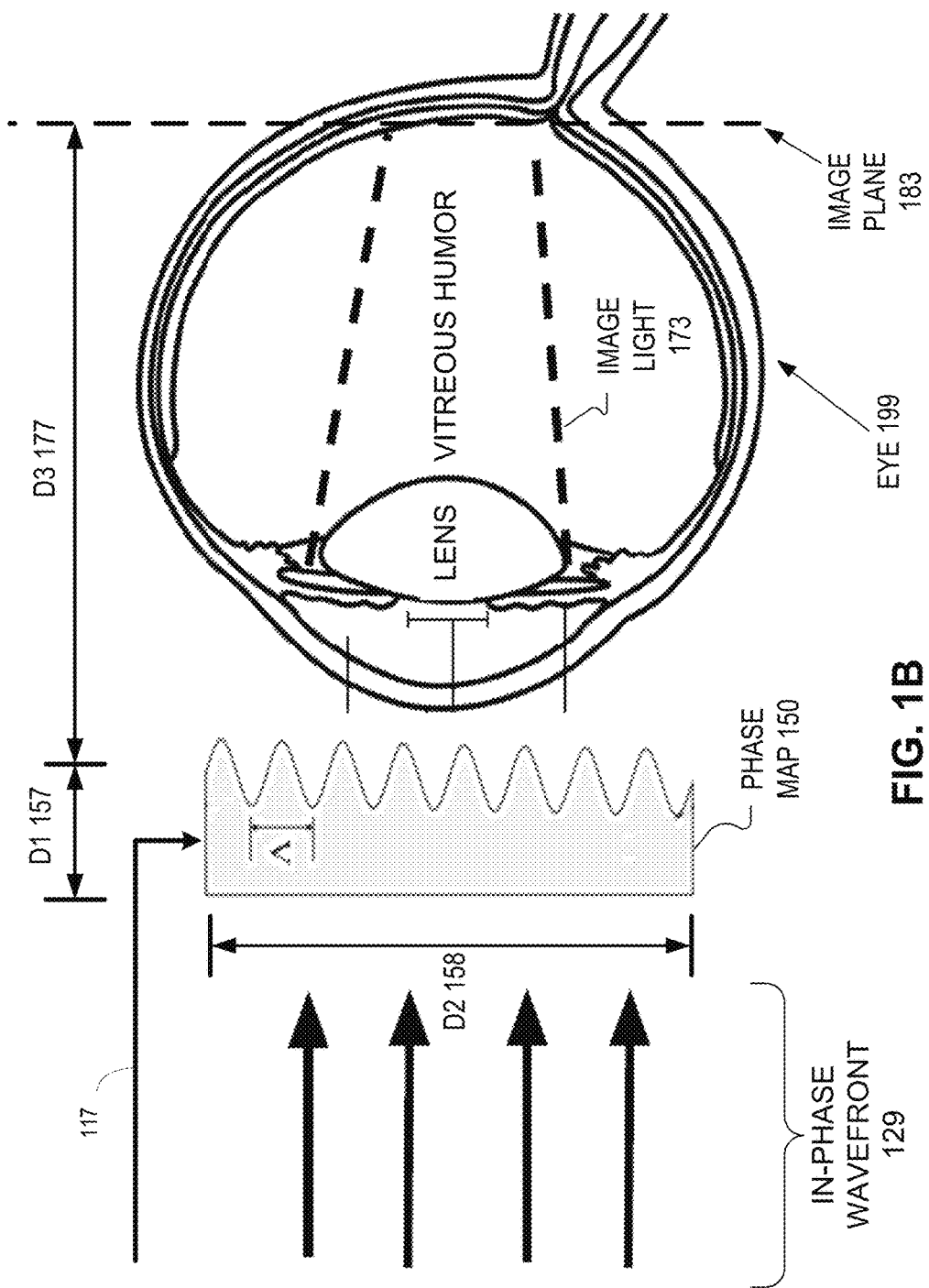
Figure 3A:
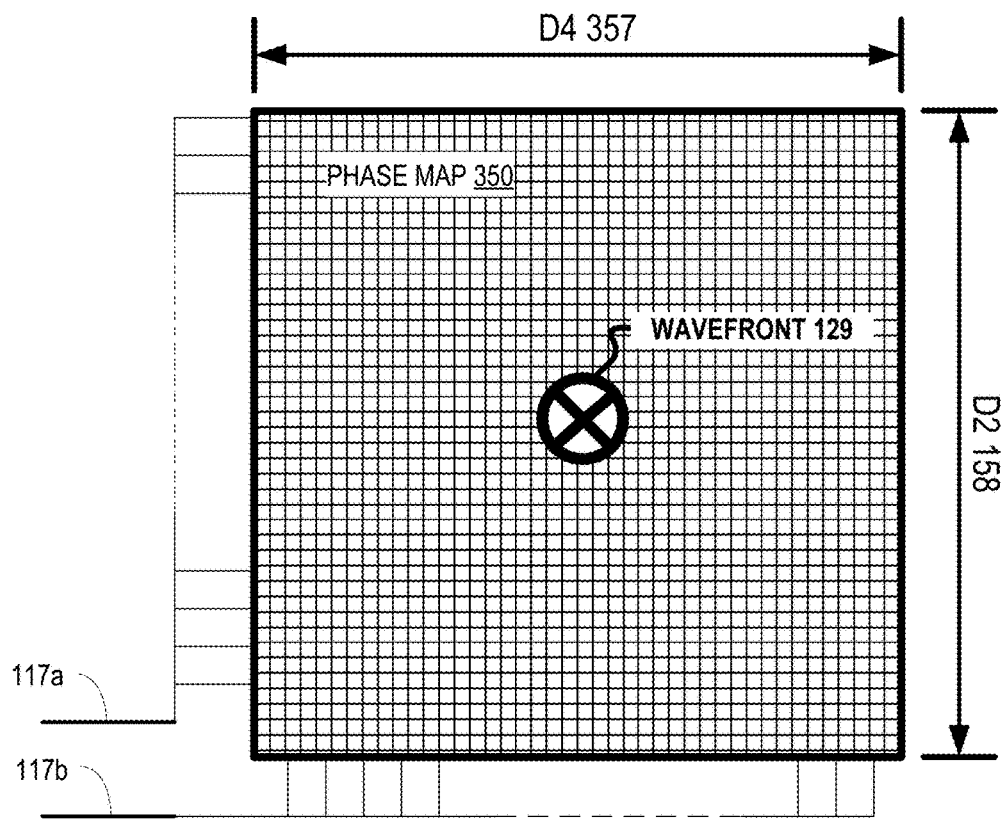
FIG. 3A illustrates an example of a programmable phase map, in accordance with an embodiment of the disclosure.

FIG. 1B shows a zoomed-in side view illustration of phase map 150 and eye 199. The disclosed phase maps are made of a transparent material, in the illustrated embodiments. In other embodiments, a phase map material is semi-translucent—e.g., where a phase map is to modulate or otherwise vary both light amplitude and light phase. The disclosed phase maps are not active reflective spatial modulators found in Liquid Crystal on Silicon (LCOS) technologies. Dimension D1 157 shows a depth of phase map 150 and dimension D2 158 shows the length of phase map 150. FIG. 3A shows a plan view of a pixelated phase map 350 (e.g., phase map 150), where phase map 350 is dimension D4 357 wide and dimension D2 158 long. A phase map 150/350 can be fabricated using an additive process (e.g. 3D printing) that builds up the depth of each pixel, or fabricated using a subtractive process (e.g. etching and photolithography) that subtracts material to define the depth of each pixel. In one embodiment, dimension D1 157 is 1 nm, dimension D2 158 is 1 mm, and dimension D4 357 is 1 mm.

In FIG. 3A, phase map 350 includes an array of transparent pixels arranged in rows and columns. In one embodiment, phase map 350 includes a 1000×1000 array of pixels where each pixel is 1 μm by 1 μm and phase map 350 is 1 mm in length (D2)×1 mm in width (D4). The pixels may be between 0.1 μm and 40 μm, in some embodiments. The pixel size may also be referred to as "phase period." In one embodiment, the pixel pitch (dimension between pixels) is non-uniform. The respective phase adjustments variously provided by pixels in the array of pixels can be selectively programmed—e.g., independently by row-wise control signals 117a and column-wise control signals 117b. Based on such programming, the respective phases of photons from in-phase wavefront 129 that encounter pixel array are changed—e.g., by pixels variously increasing or decreasing the relative phase differences between photons. In the illustrated embodiment of FIGS. 1A and 1B, in-phase wavefront 129 propagates orthogonal to the plane of phase map 150.

In FIG. 3A, wavefront 129 is illustrated as an arrow propagating into the page, although wavefront 129 may be incident on phase map 350 at different angles beside orthogonal to the plane of the phase map. Control signals 117a, 117b may operate pixels of phase map 350 to variously change, over time, phase adjustments each for a respective portion of wavefront 129. Cumulatively, varying phase with the array of pixels in phase map 350 may, at a given time, provide for diffraction of wavefront 129 to generate an image when phase map 350 is illuminated with wavefront 129. Such diffraction with phase map 350 may be changed over time—e.g., in response to control signals 117a, 117b—to generate different images at different times when phase map 350 is illuminated with wavefront 129.

Figure 3B:
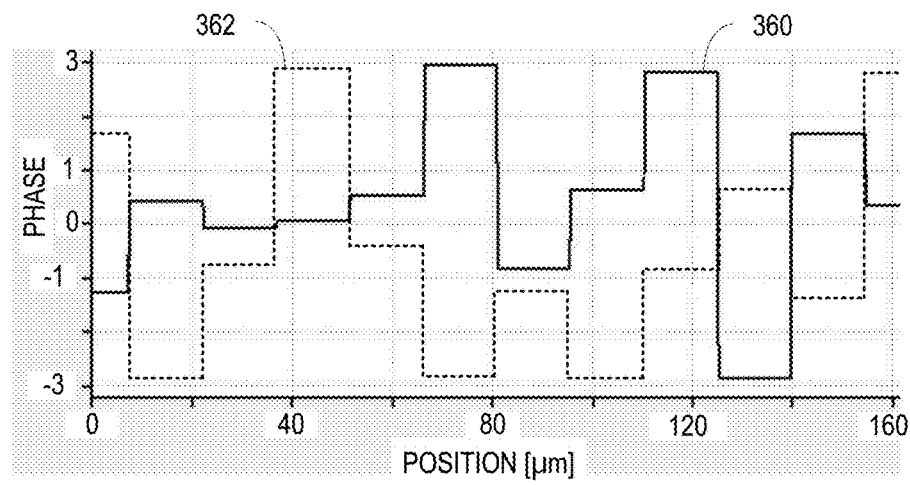
FIG. 3B illustrates phase levels of a portion of the pixels in the programmable phase map illustrated in FIG. 3A, in accordance with an embodiment of the disclosure.

One way to program a phase adjustment by a pixel is to dynamically vary an overall refractive index of the pixel. Adjusting a refractive medium of each pixel changes the propagation of light by said medium—and hence adjusts the phase of said light. FIG. 3B shows a graph including a plot 360 corresponding to an image provided by a phase map (e.g., phase map 350). Plot 360 shows, across a cross-section of ten pixels, various phase adjustments each to be provided by a respective one of such pixels to form the corresponding image. As shown in plot 360, each pixel may be programmed—e.g., by control signals 117—to provide a respective one of multiple discrete phase adjustment levels. In one illustrative embodiment, a phase pattern provided by the pixels has eight discrete phase levels. In other words, the refractive strength of pixels may be selectively set to any of eight levels. In other embodiments, the phase pattern has three or four discrete phase levels. For generating horizontally or vertically symmetrical images, two discrete phase levels may be sufficient for pixels of the phase pattern. An increased number of discrete phase levels generally corresponds to increased image quality. Although FIG. 3B illustrates discrete phase levels with sharp edges between each pixel, full grey-scale (i.e. continuous) variation of the phase levels is achievable and desirable. The graph of FIG. 3B also includes a plot 362 corresponding to another image provided by the same pixels of the same phase map. As illustrated by plots 360, 362, pixels may be selectively reprogrammed to variously provide, at different times, a different combination of phase adjustments, each combination for a different respective image.

Figure 3C:
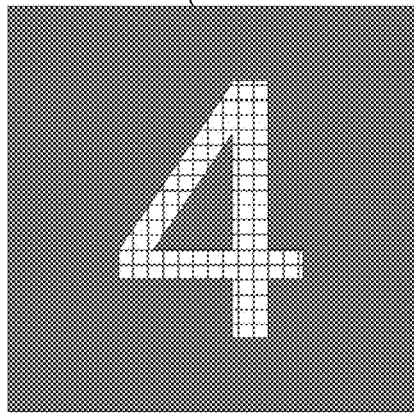
FIG. 3C illustrates images variously generated by a programmable phase map, in accordance with an embodiment of the disclosure.
Figure 3C:
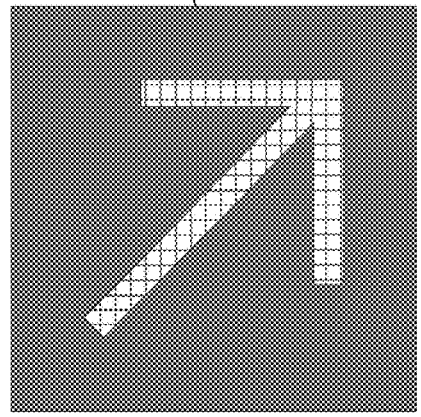
Figure 3C:
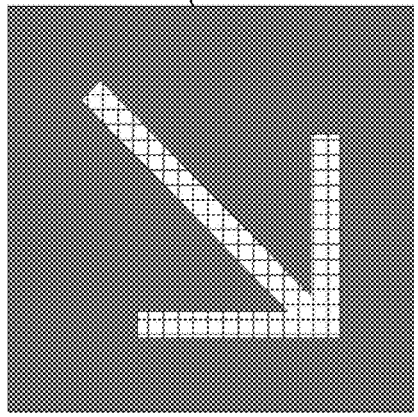
Figure 3C:
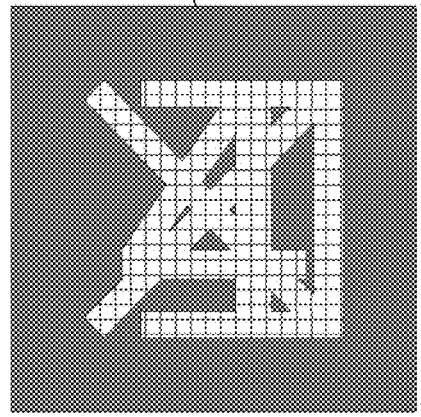

Pixels of a phase map may be variously programmed to provide different combinations of respective phase adjustments. Such different combinations may enable the phase map to variously form, at different times, different ones of images such as the illustrative image 383-386 shown in FIG. 3C. In an illustrative scenario according to one embodiment, image 383 includes the number "4," image 384 includes an arrow pointing toward a northeast quadrant, image 385 includes an arrow pointing toward a southeast quadrant and image 386 includes a superimposition of images 383-385. However, a phase map may provide any of a variety of additional or alternative images, according to different embodiments. Programming a desired combination of phase adjustments may include variously signaling pixels to diffract respective portions of wavefront 129 at different orders of diffraction to form a respective image. In response to such signaling, phase map 150 may generate, for example, one of images 383-386 on a user's retina when phase map 150 is illuminated with wavefront 129. Modification of the signaling may reprogram the pixels to instead generate a different image, such as another one of images 383-386.

Referring back to FIG. 1B, dimension D3 177 is the retina-distance between phase map 150 and image plane 183, which is targeted to be the retina of eye 199. The optical distance between phase map 150 and the retina is an important distance to define in order to determine programming of phase map 150 to form images on the retina. The internal eye optical distance between the retina and the corneal surface at the front of the eye (taking into the account the differing indices of refractions of the cornea and intervening elements such as the lens and vitreous humor of an eye) is well documented. Therefore, adding the optical distance that the phase map will be offset from the cornea to the internal eye optical distance will give the total optical distance between the phase map and image plane 183. The total optical distance may be within a range to take into account differences in eye sizes. If phase map 150 is disposed in a contact lens, the optical distance between the cornea and phase map 150 may be very small (e.g. 1 mm or less). If phase map 150 is included in a head mountable display ("HMD"), phase map 150 may be disposed 2-30 mm (or more) from the cornea.

Once the target total optical distance between the retina and the phase map is defined, input phase information (e.g., including phase patterns), to program phase map 150 for variously generating images, can be calculated using operations adapted, for example, from published algorithms or commercial optics software. Input parameters for calculating phase information to program phase map 150 may include target total optical distance, the size (length, width, and depth) of the phase map, spectral properties (e.g., including wavelength) of in-phase wavefront 129, the size of the desired real image on the retina, the integer number of phase levels to be utilized in the phase map, and the number of pixels and pixel spacing (phase period) of pixels in the phase map. After initial calculation of a phase pattern, the pattern can be altered iteratively by utilizing an inverse Fourier Transform that transforms a phase domain to an amplitude domain. The spectral properties of wavefront 129 are useful to determine phase adjustments that generate a particular image (e.g., one of images 383-386) because the diffractive pattern of the pixels is tuned to certain wavelengths, in some embodiments. The spectral properties of the in-phase wavefront may be the same as the emission (illumination light 107) of light source 105. The size of a desired image on the retina may be related to the field of view that the image will take up. In one embodiment, it is desirable for the image formed on the retina to be approximately 20% of a field of view of the user/wearer of the near-eye display 100.

With the input parameters recited above, near-eye display 100 can be modeled by commercial software and the phase map can be iteratively adjusted (using iterative inverse Fourier Transforms) to improve images generated by the phase map. VirtualLab™ by LightTrans GmbH of Jena Germany is one software suite that could model near-eye display 100.

Figure 2:
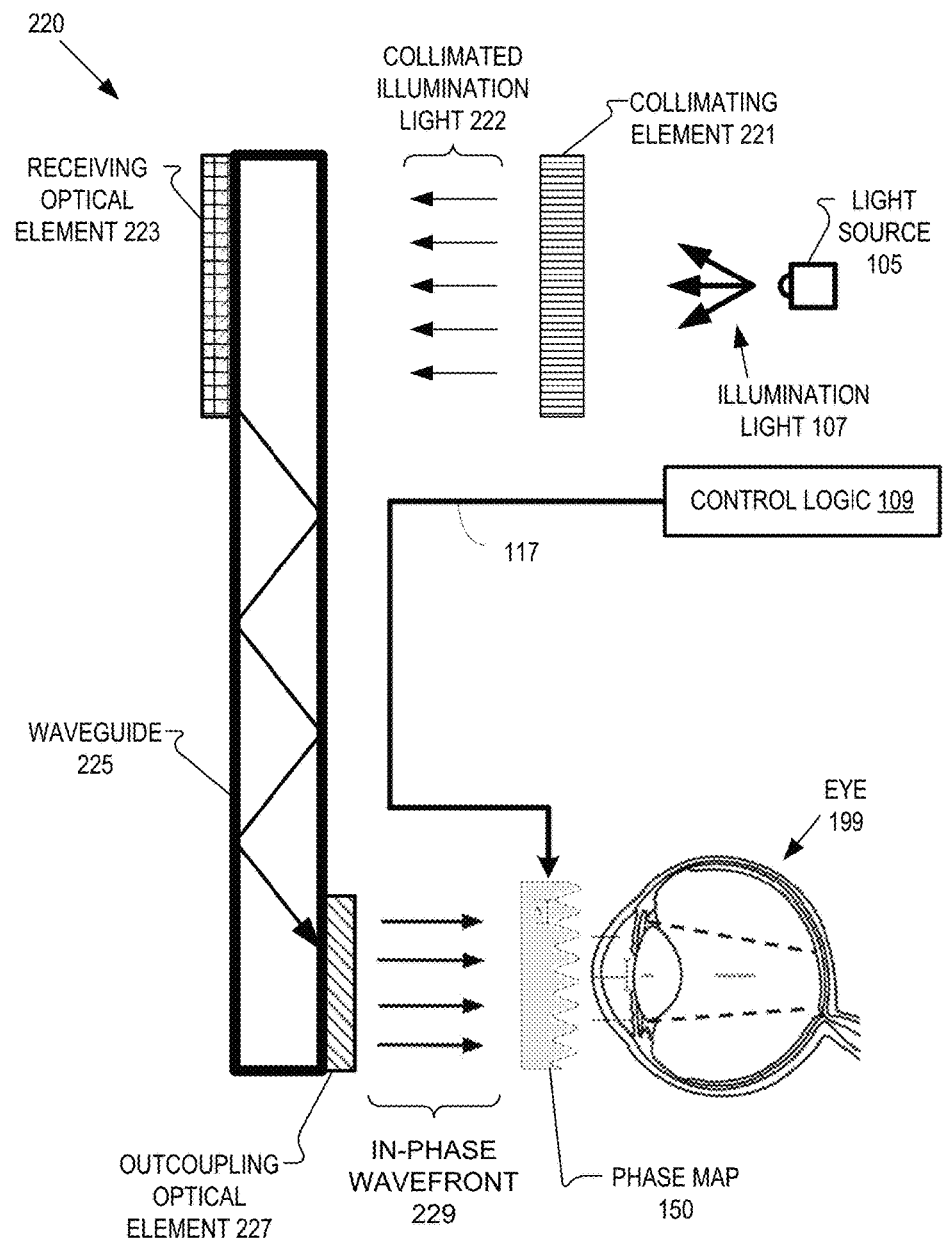
FIG. 2 illustrates an example near-eye display that includes a programmable phase map, in accordance with an embodiment of the disclosure.

FIG. 2 illustrates an example near-eye display 200 that includes a phase map 150, in accordance with an embodiment of the disclosure. FIG. 2 shows an example optical system 220 that is one example of optical system 120. Optical system 220 includes collimating element 221, receiving optical element 223, waveguide 225, and outcoupling optical element 227. In FIG. 2, collimating element 221 is disposed between light source 105 and waveguide 225. Collimating element 221 collimates illumination light 107. Collimating element 221 includes a Fresnel lens, in one embodiment. Receiving optical element 223 receives collimated illumination light 222 and directs collimated illumination light 222 to propagate through waveguide 225. Waveguide 225 is fabricated from a suitable transparent material (e.g. acrylic). In one embodiment, waveguide is only 1 μm thick and 1 mm wide. Waveguide 225 may rely on Total Internal Reflection ("TIR") or mirror elements to guide the illumination light as the illumination light propagates through waveguide 225. In one embodiment, receiving optical element 223 includes a Bragg grating configured to redirect the illumination light so that the illumination light propagates through waveguide 225 at the proper angle (that does not violate the principles of TIR, for example). In FIG. 2, receiving optical element 223 is a reflective optical element, but it is understood that receiving optical element 223 may also be a transmissive optical element in some embodiments.

Outcoupling optical element 227 is configured to outcouple the illumination light propagating through waveguide 225 and direct the illumination light to the phase map guide 225 as in-phase wavefront 229. Outcoupling optical element 227 may be a Bragg grating. Outcoupling optical element 227 is integrated into the bulk medium of waveguide 225 as a volume hologram, in one embodiment. Receiving optical element 223 may also be integrated into the bulk medium of waveguide 225 as a volume hologram. Outcoupling optical element 227 directs in-phase wavefront 229 to phase map 150 at the proper incident angle. In one embodiment, in-phase wavefront is in-phase because waveguide 225 is phase preserving and it preserves the in-phase nature of illumination light 107 generated by light source 105 (which may be approximately modeled as a point source). In one embodiment, in-phase wavefront 229 is in-phase because outcoupling optical element is phase selective and outputs only illumination light propagating in waveguide 225 that is in-phase. One important function of optical system 220 is to deliver a predictable, in-phase wavefront 129 because phase map 150 functions optimally when it is illuminated by a wavefront for which it was designed. Although in-phase wavefront 129/229 is illustrated as collimated, in-phase wavefront 129/229 may be converging or diverging, in some embodiments.

Near-eye display 200 may include control logic 109 coupled to provide signals 117 to phase map 150. Although certain embodiments are not limited in this regard, signals 117 may be exchanged via respective signal lines that are coupled to and/or extend along a side of waveguide 225 (or other such means for propagating collimated illumination light 222). For each of multiple pixels of phase map 150, the pixel may be coupled to receive both a respective one of signals 117 and a respective portion of in-phase wavefront 229. Based on signaling from control logic 109, the pixel may variously adjust a phase of the received portion of in-phase wavefront 229. Such control may enable different images to be variously provided from phase map 150 to a same region of the retina of eye 199. For example, providing of a first image (e.g., image 383) at a first time may include phase map 150 providing a first difference between wavefront phase adjustment by a first pixel and wavefront phase adjustment by a second pixel. By contrast, providing of a second image (e.g., image 384) at a different time may include phase map 150 providing a second difference—e.g., other than the first difference—between wavefront phase adjustment by the first pixel and wavefront phase adjustment by the second pixel.

Conventional wearable near-eye displays typically include a micro-display and an image relay to variously direct an image formed on the display onto the eye. Near-eye displays include head mountable displays. However, this approach requires the optics (e.g. mirrors and lenses) of the image relay to direct an image to the eye without distorting the image or shifting the colors of the image because the image directed to the eye and the pixels of the micro-display have a one-to-one correspondence. Conventional wearable displays rely on amplitude modulation of the light to generate the image for viewing. The image relays to deliver an image from the micro-display to the eye are three-dimensional relays that add unwanted bulk to the wearable display. Additionally, the fabrication and assembly of precision optical components to maintain image quality adds expense to the wearable displays. In contrast, the disclosed near-eye displays utilize a phase map that does not have a one-to-one correspondence between the pixels of the phase map and images to be formed directly on the retina of the eye. Rather, the entire phase map collectively modulates the phase (e.g., in some embodiments, rather than amplitude) of the in-phase wavefront to form the images on the retina. Phase map may modulate localized amplitudes of the in-phase wavefront in addition to the phase, in some embodiments. Since the image formation happens at the phase map and image light 173 only has to travel from the phase map to the retina, a bulky and expensive three-dimensional image relay is not required to direct images to the eye. Instead, a two-dimensional (very thin) waveguide is all that is required to guide illumination light 107 to illuminate phase map 150 because the waveguide does not need to guide image light as image light 173 is only formed after phase map 150.

Conventional near-eye displays must also spend significant optical resources on ensuring that the user/wearer of the near-eye display can actually focus on the image generated by the micro-display (e.g. LCD or LCOS). In the disclosed near-eye displays, the focusing ability (accommodation) of a human eye is not an obstructing design challenge as real images can be variously formed, at different times, directly onto the retina from the phase map and any required magnification can be accounted for directly in the programming of a phase pattern for the phase map. Therefore, additional focusing optics are not required to allow a wearer to focus on the image and the phase map can be the last optical element that assists in forming images onto the eye. Additionally, a user's prescription (for contact lenses or eye glasses) can be a parameter of phase pattern programming so that the optical power required to present images that the wearer/user perceives as in-focus is accommodated in the programming of the phase map—e.g., by signals 117. Yet another potential advantage of the disclosed near-eye displays is that phase maps are an efficient image delivery vehicle in that most (or almost all) of the light emitted by the light source is utilized to variously form different images. In contrast, the filters, polarizers, and liquid crystal of conventional micro-displays block or wastes a significant amount of light injected into the micro-displays to form an image.

Figure 4:
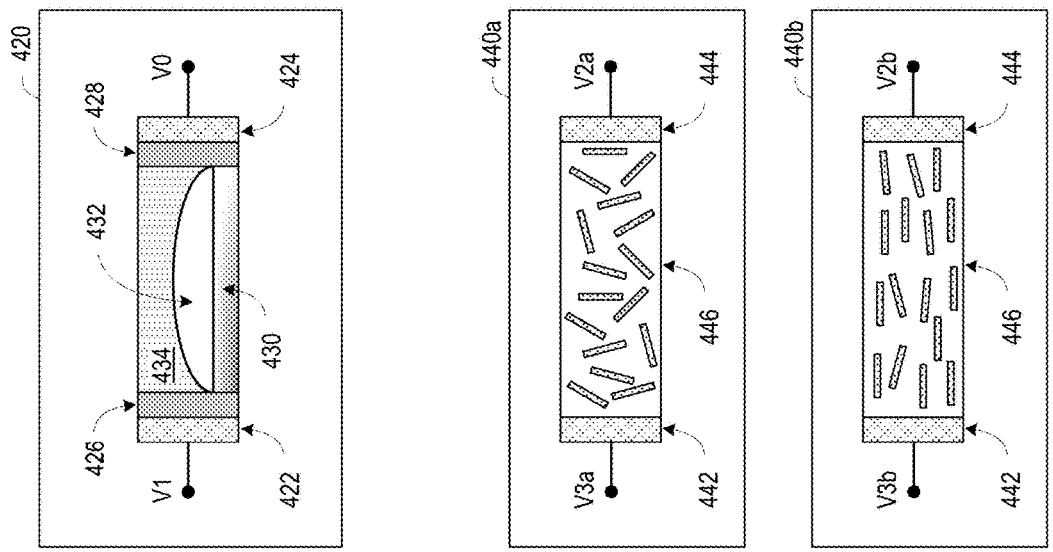
FIG. 4 illustrates an example of a programmable phase map, in accordance with an embodiment of the disclosure.
Figure 4:
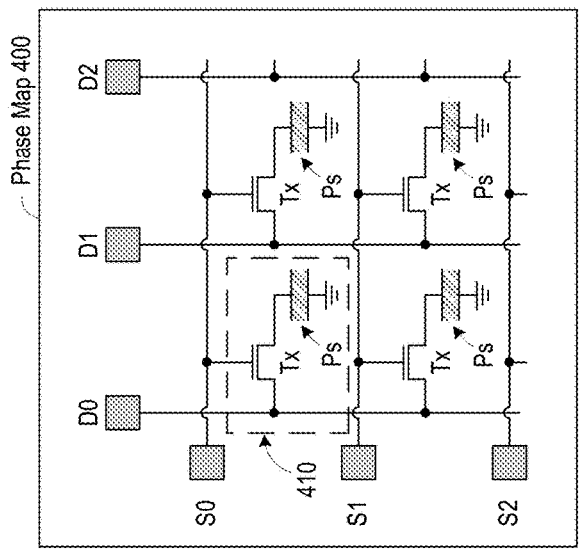

FIG. 4 shows a circuit diagram of a phase map 400 to variously form images on a retina according to an embodiment. Phase map 400 may include some or all of the features of phase map 150 or phase map 350, for example. Phase map 400 may include pixels—e.g., including a pixel 410—variously coupled each to a respective one of select inputs (e.g., including inputs S0, S1,S2) and respective one of data inputs (e.g., including inputs D0, D1, D2). Inputs S0, S1, S2 may variously enable selection of a row of pixels, where such selection enables control of pixels of the row, via inputs D0, D1, D2, to variously provide respective amounts of phase adjustment with such pixels. In one illustrative embodiment, control signals 117 are variously provided to respective ones of inputs S0, S1, S2 and inputs D0, D1, D2.

In the embodiment shown, phase map 400 includes an active matrix architecture, such as one including a thin-film transistor (TFT) array, wherein each pixel includes a respective transistor Tx and a respective phase shift element Ps. Such pixels may further comprise one or more storage capacitors and/or other circuit elements (not shown) that, for example, have a configuration adapted from any of a variety of conventional display matrix architectures. In an alternate embodiment, phase map 400 includes circuit structures adapted from any of a variety of conventional passive matrix architectures.

FIG. 4 further shows, in cross-sectional view, one example of a cell 420 of a phase map according to an embodiment. Cell 420, which may be one of phase shift elements Ps, is an example of an element providing an electrowetting mechanism to adjust light phase according to an embodiment. For example, cell 420 may be configured to transmit light through a transparent substrate 430, such as glass, and further through fluids 432, 434 (e.g., an oil and an aqueous solution, respectively) that form a hydrophobic interface. Application of a voltage differential across electrodes 422, 424 may result in distortion of the interface between fluids 432, 434. A thickness profile of fluids 432, 434 across the surface of substrate 430 may thus be selectively manipulated, as well as a corresponding phase adjustment for light transmitted through fluids 432, 434. Although some embodiments are not limited in this regard, cell 420 may further comprise dielectrics 426, 428—e.g., including barium strontium titanate (BST)—to aid in maintaining a voltage difference across fluids 432, 434.

FIG. 4 further shows two cross-sectional view 440a, 440b each of a respective state of an element—e.g., a Ps of phase map 400—providing a liquid crystal (LC) mechanism to adjust light phase according to an embodiment. As shown in cross-sectional view 440a, the element may include a LC cell 446 disposed between electrodes 442, 444 each coupled to receive a respective voltage. LC cell 446 may include any of a variety of liquid crystal materials adapted from conventional LC display technologies—e.g., including nematic liquid crystal materials such as cyanobiphenyls, cholesteric liquid crystal materials such as hydroxypropyl cellulose and cholesteryl benzoate, and/or the like. At a time represented by view 440a, voltages V3a, V2a applied across the LC cell 446 may allow for individual LC molecules to be relatively non-aligned. By contrast, at a time represented by view 440b, a relatively large voltage differential applied across the LC cell 446 (e.g., by voltages V3b, V2b) may allow for increased alignment of LC molecules with each other and/or with respect to a line of direction between electrodes 442, 444. The degree of alignment of LC molecules may change a refractive index of LC cell 446, as well as a corresponding amount of phase adjustment by LC cell 446.

Figure 5A:
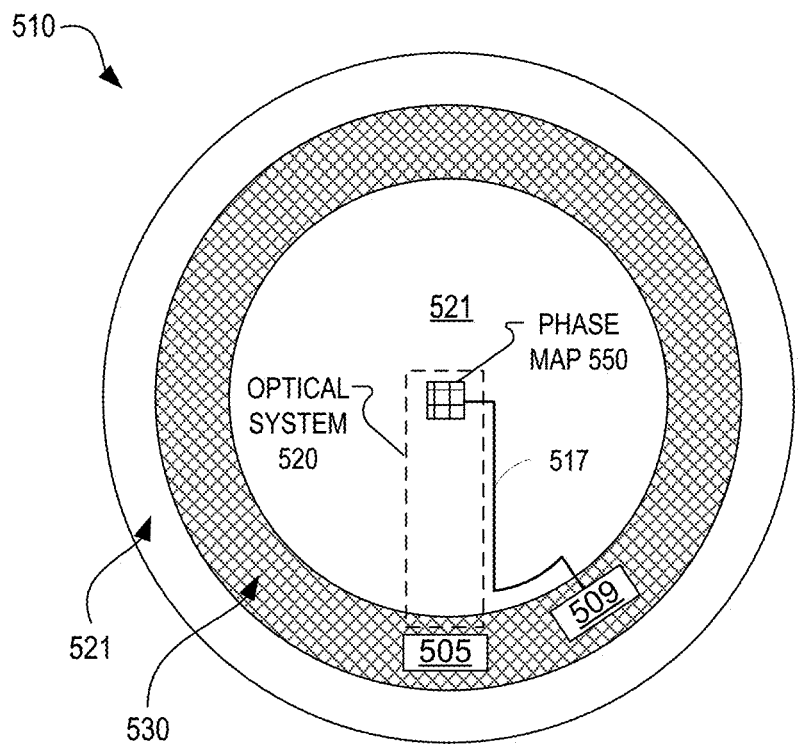
FIGS. 5A and 5B illustrate a contact lens that includes a light source and a phase map for variously generating images directed into the eye of a wearer of the contact lens, in accordance with an embodiment of the disclosure.

FIG. 5A illustrates a top view of a smart contact lens ("SCL") 510 that includes control circuitry 509, light source 505, optical system 520, and phase map 550, in accordance with an embodiment of the disclosure. SCL 510 is one example of a wearable near-eye display that includes a phase map. SCL 510 includes transparent material 521 that is made from a biocompatible material suitable for a contact lens. Substrate 530 is illustrated as a substantially flattened ring disposed atop or embedded within transparent material 521. In one embodiment, the flattened ring has a diameter of about 10 millimeters, a radial width of about 1 millimeter, and a thickness of about 50 micrometers.

Substrate 530 includes one or more surfaces for mounting electrical or elements such as control circuitry 509 and light source 505. In one embodiment, substrate 530 includes a semiconductor material (e.g. silicon) and control circuitry 509 is formed in substrate 530 by way of common CMOS processes. Control circuitry 509 (e.g., providing functionality of control logic 109) may be an arrangement of discrete logic or a microprocessor, for example. In one embodiment, substrate 530 includes a multi-layer flexible circuit board. In one embodiment, substrate 530 is made of a rigid material such as polyethylene terephthalate ("PET"). In one embodiment, substrate 530 is made of flexible material such as polyimide or organic material. Substrate 530 may be disposed along an outer perimeter of SCL 510 so as not to interfere with a viewable region of SCL 510 that a wearer of SCL 510 would be looking through. However, in one embodiment, substrate 530 is substantially transparent and does not substantially interfere with a wearer's view, regardless of disposition location.

Figure 5B:
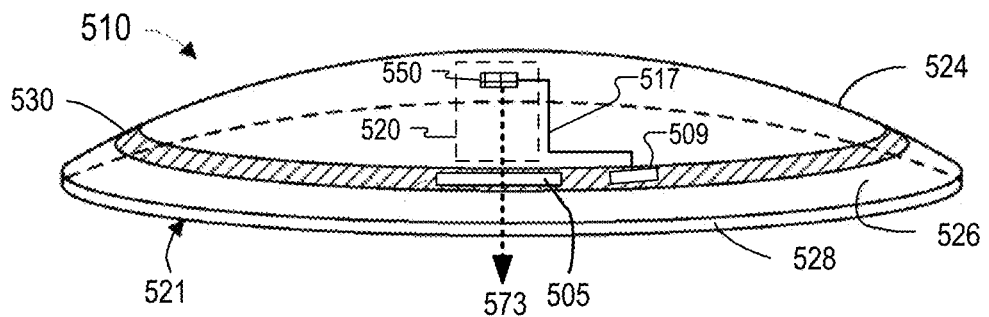

FIG. 5B illustrates a side view of a SCL 510 that includes control circuitry 509, light source 505, optical system 520, and phase map 550, in accordance with an embodiment of the disclosure. FIG. 5B shows transparent material 521 has a concave surface side 526 (eyeside) opposite a convex surface side 524 (external side). Concave surface side 526 will have substantial contact with the eye of a wearer of SCL 510. A circular outside edge 528 connects concave surface side 526 and convex surface side 524.

When control circuitry 509 activates light source 505, light source 505 injects illumination light into optical system 520 which delivers an in-phase wavefront to phase map 550. Control circuitry 509, or other such control logic of SCL 510, may further provide signals 517 (e.g., signals 117) to variously program, at different times, different phase patterns of phase map 550. Based on signals 517, phase map 550 may variously diffract the in-phase wavefront as image light 573 (by manipulating the phase of the in-phase wavefront) in an eyeward direction to variously form, at different times, various real images each on the retina of a wearer of SCL 510. SCL 510 may be weighted using similar techniques as contacts that are designed for astigmatisms to keep phase map 550 in a consistent location and maintain a spatial orientation relative to the eye so the images are formed with a specific orientation.

Figure 7A:
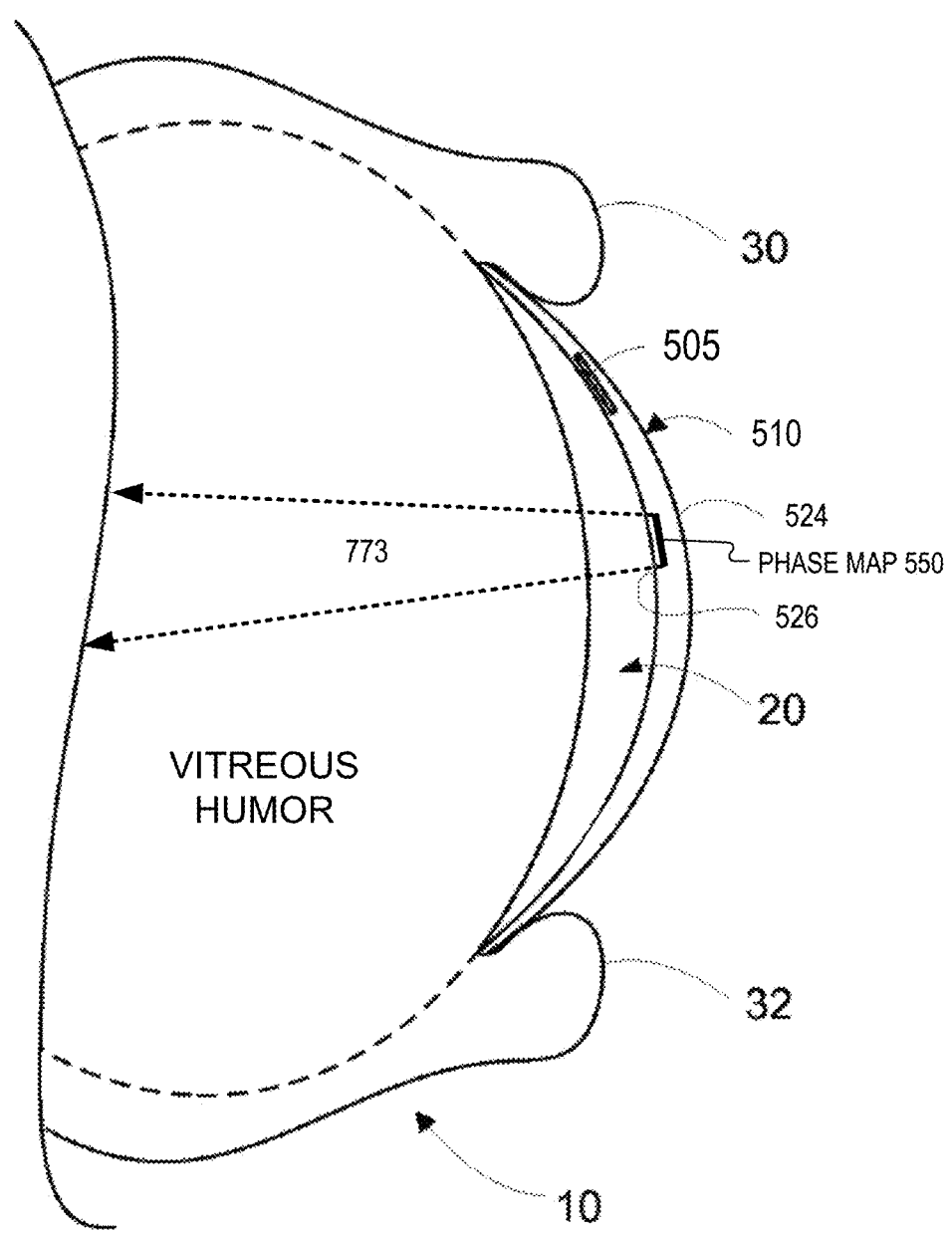
FIGS. 7A and 7B illustrate a contact lens that includes a programmable phase map in an eye, in accordance with an embodiment of the disclosure.
Figure 7B:
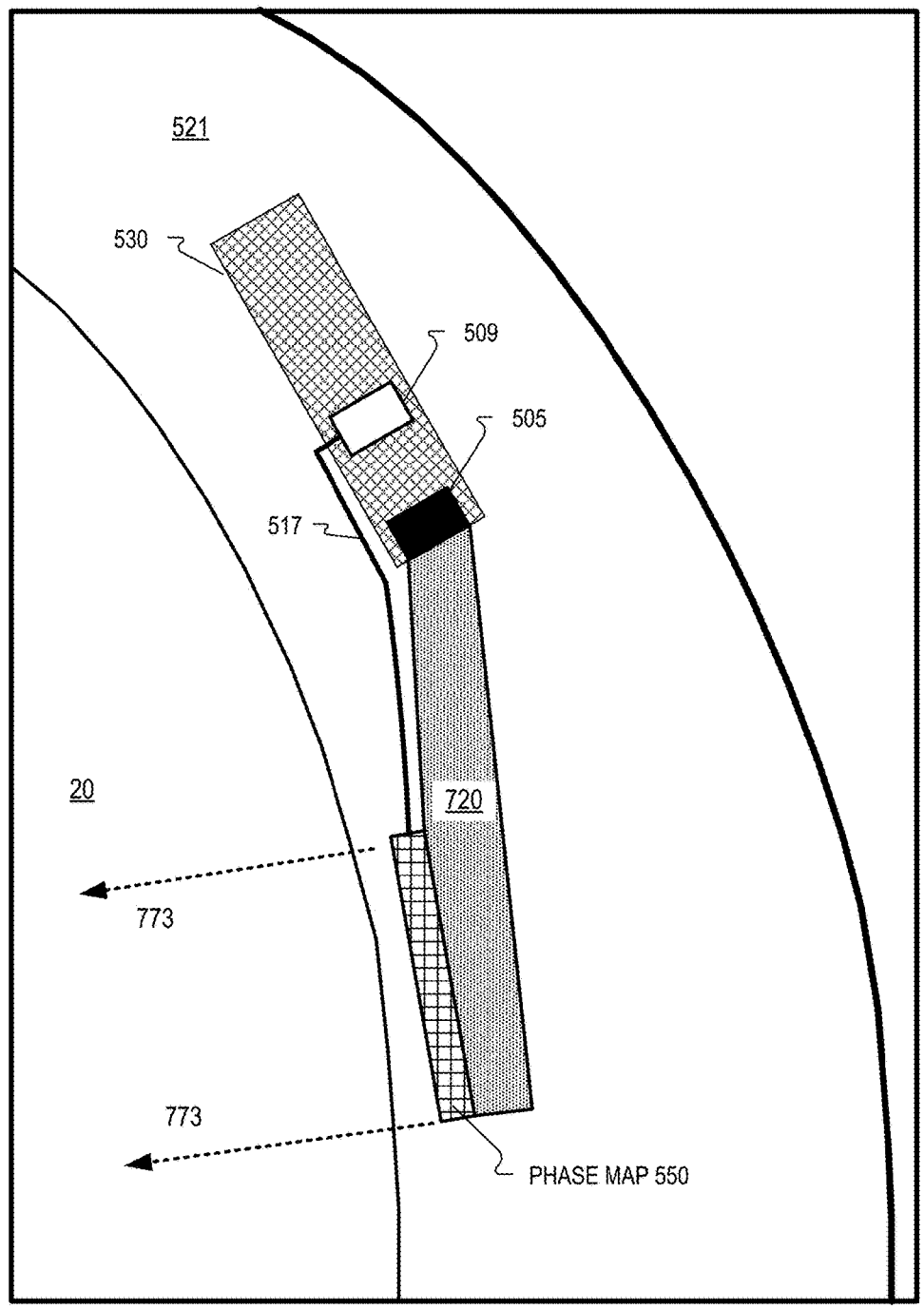

FIG. 7A illustrates a cross-section side view of an example SCL 510 mounted on a corneal surface 20 of an eye 10, in accordance with an embodiment of the disclosure. SCL 510 is shown mounted under upper eyelid 30 and lower eyelid 32. FIG. 7B illustrates a zoomed-in view of light source 505, optical system 520, and phase map 550, in accordance with an embodiment of the disclosure. Light source 505 and optical system 520 are disposed on an inner edge of substrate 530, where light source 505 is to inject illumination light into optical system 720 and control circuitry 509 is to variously program phase patterns of phase map 505 with signals 517. Optical system 720 delivers an in-phase wavefront to phase map 550. In an embodiment, conductive traces to communicate signals 517 extend on a surface of optical system 720. Based on a given phase pattern programmed using signals 517, phase map 550 may scatter the in-phase wavefront as image light 773 in an eyeward direction, where image light 773 forms a corresponding one of various real images on the retina of a wearer of SCL 510.

Using the elements of near-eye display 100/200 in a contact lens offers many potential advantages. First, since image light 573/673 is formed at phase map 550, a bulky light delivery relay is not required to deliver images from a micro-display to the eye. This allows a waveguide in optical system 720 to be very thin (two-dimensional) since it need not be designed to maintain images propagating from a micro-display. Rather, optical system must merely deliver illumination light from light source 505 to phase map 550 as an in-phase wavefront. Additionally, phase map 550 itself can be very thin (e.g. 1 µm deep) since it modulates the phase of the in-phase wavefront rather than exclusively relying on pure amplitude modulation of light to variously form images. Furthermore, modulating the phase of the in-phase wavefront also allows phase map 550 to be transparent which will be less noticeable to a wearer of SCL 510 if phase map 550 is located (at least partially) in a field of view of the wearer.

Figure 6:
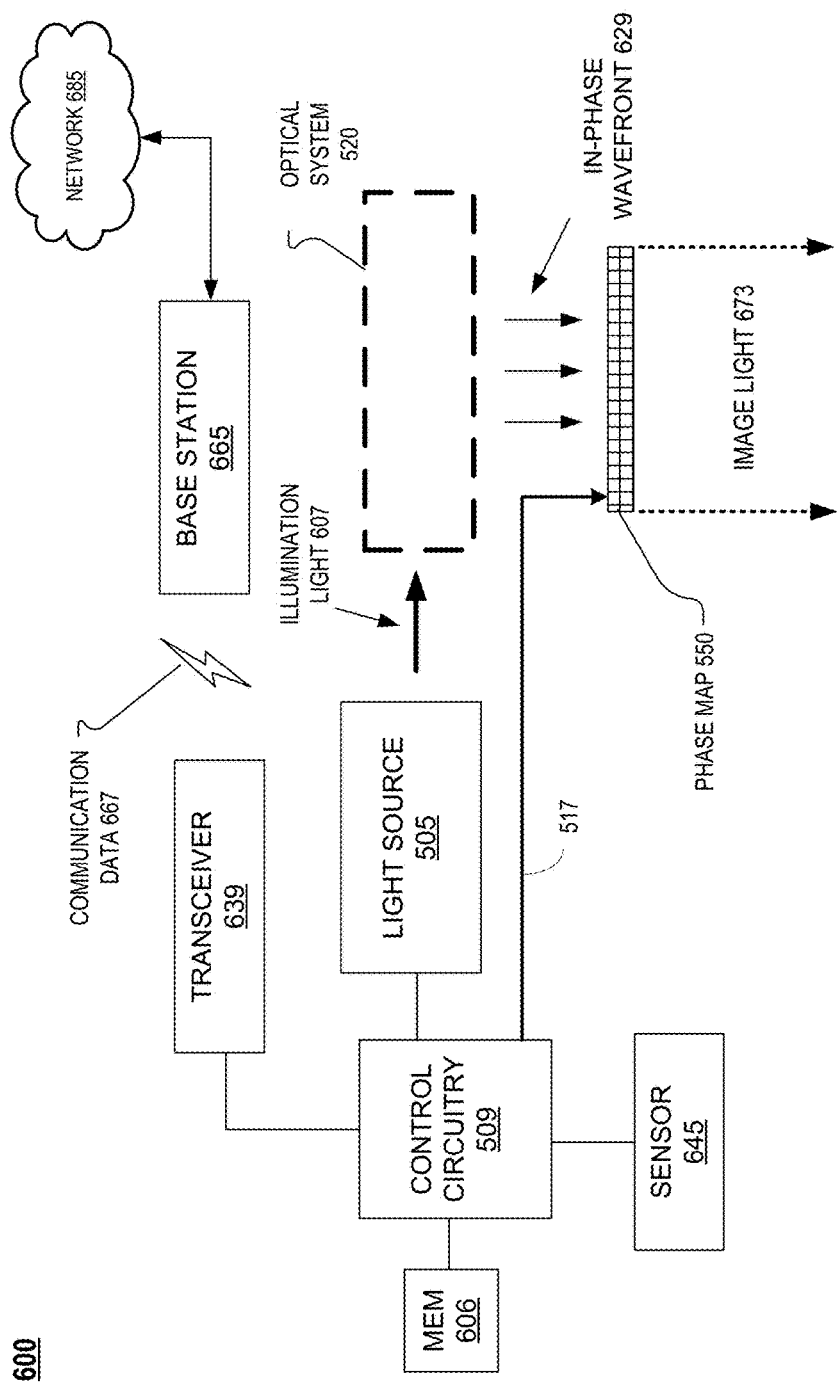
FIG. 6 illustrates a system that includes a near-eye display, in accordance with an embodiment of the disclosure.

FIG. 6 illustrates a system 600 that includes a near-eye display, in accordance with an embodiment of the disclosure. System 600 includes a near-eye display that includes light source 505, optical system 520, and phase map 550. System 600 also includes light control circuitry and logic 509, memory 606, sensor 645, and transceiver 639. System 600 also includes a base station 665 that is coupled to communicate with a network 685. Network 685 may be a wireless cellular network, Wide Area Network ("WAN"), Local Area Network ("LAN"), or otherwise. System 600 also includes a power source (not illustrated) to power the illustrated elements. The power source may include a battery and/or a photovoltaic element that generates electrical power by harvesting light.

In system 600, control circuitry 509 is coupled to light source 505 to selectively modulate illumination light 607 emitted by light source 505. To turn on light source 505, control circuitry 590 may send a digital signal to a control terminal of a transistor that regulates the current through light source 505, for example. Control circuitry 509 is coupled to read and write to memory 606. Memory 606 may store instructions for execution on control circuitry 509. Control circuitry 509 is coupled to initiate a measurement or test by sensor 645. Sensor 645 is coupled to send the measurement or the results of the test to control circuitry 509. Sensor 645 may measure biometric data. In one embodiment, sensor 645 is a miniaturized glucose meter. Sensor 645 is disposed on substrate 530 in one embodiment of contact lens 510.

Transceiver 639 is positioned to receive communication data 667 from base station 665. Base station is a network router, in one embodiment. Control circuitry 509 is coupled to read an output of transceiver 639 and coupled to transmit data to transceiver 639 to be sent to base station 665. Communication between transceiver 639 and base station 665 may be WiFi, BlueTooth™, or other wireless communication standards or protocols. Control circuitry 509 may initiate an action in response to receiving communication data 667 from transceiver 639. For example, communication data 667 may be a digital word that instructs control circuitry 509 to activate (turn on) light source 505 in order to illuminate phase map 550 and generate various images for the eye of a user of system 600. Control circuitry 509 may also initiate a measurement using sensor 645 in response to certain communication data 667. In one embodiment, control circuitry 509 activates light source 505 to generate image light 673 in response to receiving a measurement from sensor 645 that is above or below a given threshold. Control circuitry 509 may further provide signals 517 to variously program different phase patterns of phase map 550 over time. Where sensor 645 is a glucose sensor, control circuitry 509 may activate light source 505 in response to a low glucose reading to form images onto the retina of a user. The images may alert the user that her blood sugar may be low. System 600 (excluding base station 665) may be implemented into a contact lens or HMD, in accordance with embodiments of the disclosure.

Figure 8:
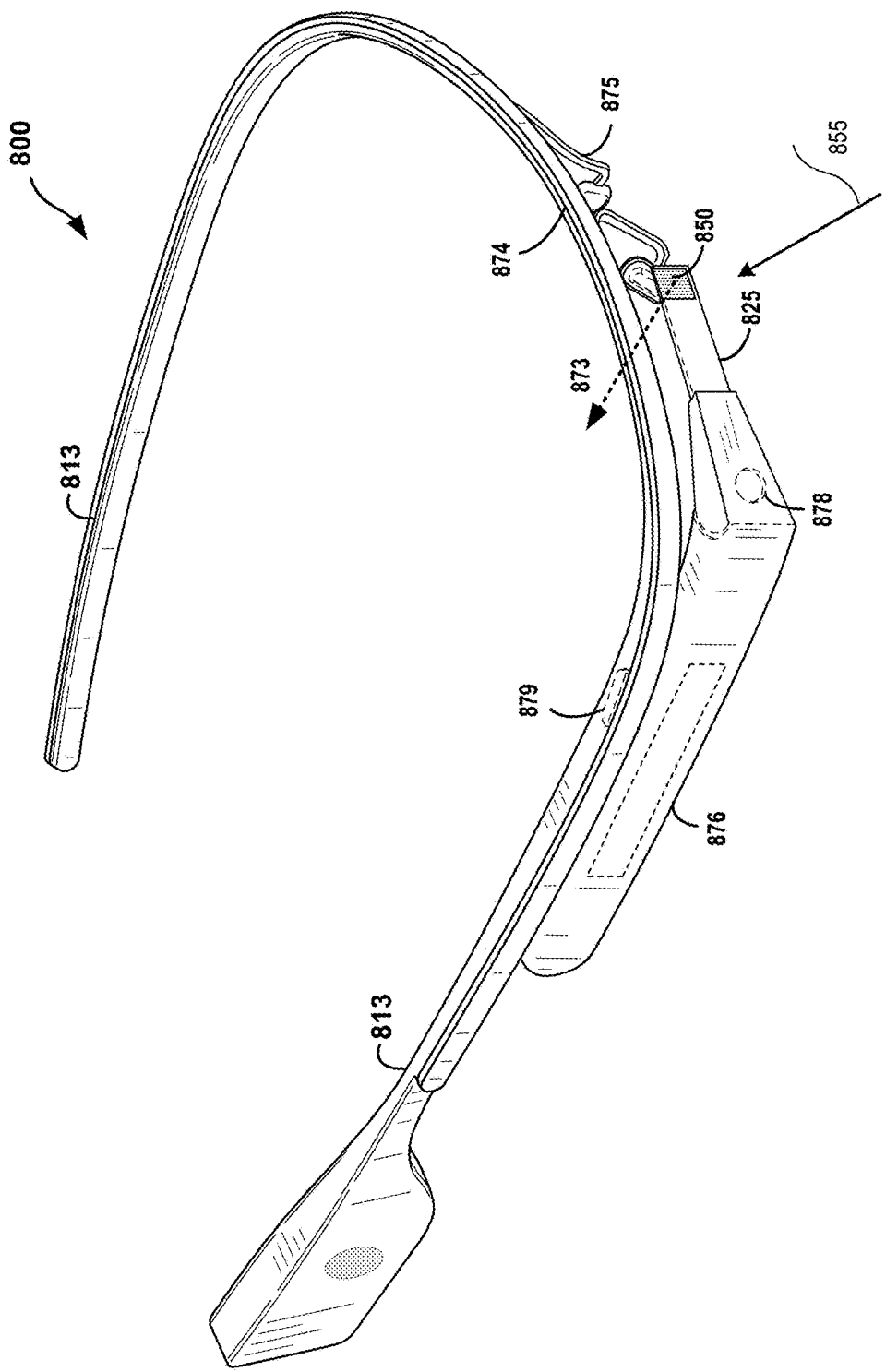
FIG. 8 illustrates a head mountable display that includes a programmable phase map, in accordance with an embodiment of the disclosure.

FIG. 8 illustrates a head mountable display ("HMD") that may integrate portions of system 600, in accordance with an embodiment of the disclosure. Example HMD 800 is a monocular HMD. HMD 800 includes side-arms 813, a center frame support 874, and a bridge portion with nosepiece 875. In the example embodiment shown in FIG. 8, center frame support 874 connects the side-arms 813. HMD 800 does not include lens-frames containing lens elements in the illustrated embodiment, but other embodiments may include lens elements. An HMD is a display device worn on or about the head. Although FIG. 8 illustrates a specific monocular HMD 800, embodiments of the present invention are applicable to a wide variety of frame types and styles (e.g. visor, headband, goggles).

HMD 800 may additionally include a component housing 876, which may include an on-board computing system (not shown), an image capture device 878, and a button 879 for operating the image capture device 878 (and/or usable for other purposes). Component housing 876 may also include other electrical components and/or may be electrically connected to electrical components at other locations within or on the HMD. Component housing 876 may include light sources (not shown) positioned to inject waveguide 825 will illumination light. As discussed previously, waveguide 825 can be include in an optical system that deliver an in-phase wavefront to phase map 850. Control circuitry (not shown) disposed in component housing 876 may be coupled to program different phase patterns of phase map 850 at different times. While programmed with a given phase pattern, phase map 850 may adjust the phase of the in-phase wavefront to generate image light 873. Although not specifically illustrated, the components of optical system 220 may be integrated, as needed, into HMD 800 to generate image light 873 via phase map 850.

Here again, using a phase map in a near-to-eye display allows waveguide 825 to be very thin when compared to larger image relays in conventional HMDs. And, the illustrated embodiment of HMD 800 is capable of displaying an augmented reality to the user since waveguide 825 and phase map 850 may be transparent and permit the user to see a real world image via external scene light 855 in addition to image light 873.

Figure 9:
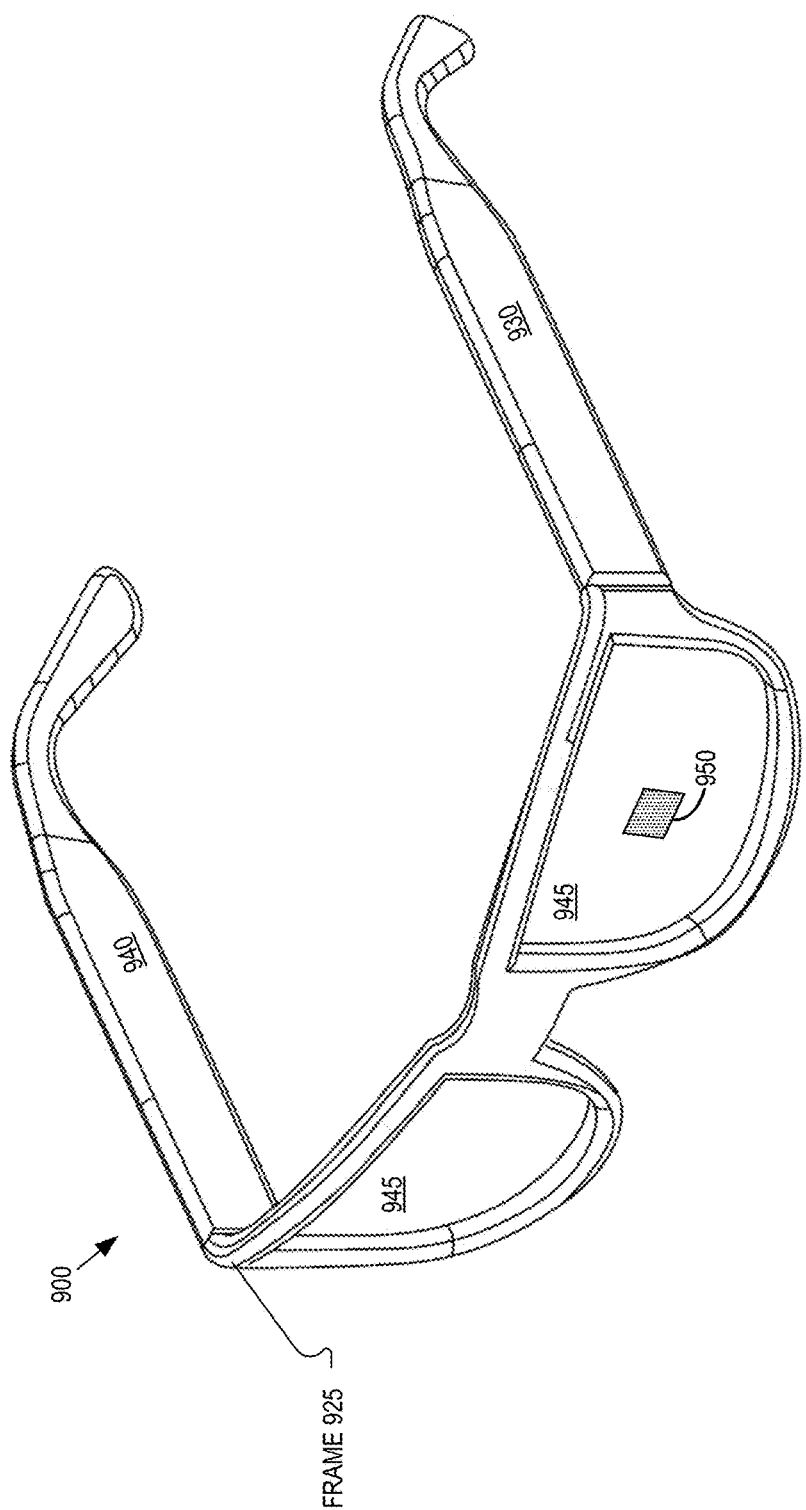
FIG. 9 illustrates eyeglasses that include a programmable phase map, in accordance with an embodiment of the disclosure.

FIG. 9 is a perspective view of example wearable glasses 900 (one example of an HMD) that may include portions of system 600, in accordance with an embodiment of the disclosure. The illustrated embodiment of wearable glasses 900 includes lenses 945 disposed in frame 925 that includes left temple arm 930 and right temple arm 940. A phase map 950 is included with one of the lenses 945, in the illustrated embodiment. In one embodiment, both lenses 945 include a phase map and corresponding optical system to deliver an in-phase wavefront to the phase maps so that each eye receives respective images from the corresponding phase map. Phase map 950 may be planar or curved according to the curvature of lens 945. Although FIG. 9 illustrates a traditional eyeglass frame 925, embodiments of the disclosure are applicable to a wide variety of frame types and styles (e.g. visor, headband, goggles). The frame 925 of eyeglasses 900 may also include other electrical components and/or may be electrically connected to electrical components at other locations within or on eyeglasses 900. Frame 925 may include light sources (not shown) positioned to inject a waveguide (not illustrated) will illumination light to illuminate phase map 950. As discussed previously, the waveguide can be included in an optical system that delivers an in-phase wavefront to phase map 950—e.g., where phase map 950 is programmable to variously adjust the phase of the in-phase wavefront to generate image light directed toward an eye of a wearer of eyeglasses 900. Although not specifically illustrated, the components of optical system 220 may be integrated, as needed, into eyeglasses 900 to generate image light via phase map 950.

Multiple programmable phase maps 950 may be included in one lens 945 of eyeglasses 900. In one example, each of the multiple phase maps 950 in one lens 945 may have their own waveguide and light source. Each light source can be selectively activated to illuminate (via its corresponding waveguide) its corresponding phase map to selectively display a respective variety of images into the eye. The multiple phase maps may be configured in the lenses 945 to increase the effective eye box of the near-to-eye display. Multiple phase maps may be incorporated into the various near-to-eye displays 510 and 800.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A near-to-eye display comprising:
  a light source to emit illumination light;
  an optical system configured to receive the illumination light from the light source and output the illumination light as an in-phase wavefront;
  a phase map including multiple pixels each positioned to receive a respective portion of the in-phase wavefront, wherein the multiple pixels are configured to collectively spatially modulate a phase of the in-phase wavefront; and
  control logic including circuitry coupled to the phase map to generate different phase patterns with the phase map by configuring a phase adjustment amount of the multiple pixels, each of the different phase patterns to form a respective image at a retina-distance from the phase map as the in-phase wavefront propagates through the phase map in response to being illuminated by the in-phase wavefront.

2. The near-to-eye display of claim 1, wherein the phase adjustment amount of each of the multiple pixels is independently configurable, and wherein the control logic is coupled to independently configure the phase adjustment amount of each of the multiple pixels.

3. The near-to-eye display of claim 1, wherein the multiple pixels of the phase map includes a first pixel and a second pixel, and wherein the control logic is coupled to the phase map to perform operations including:
generating a first phase pattern included in the different phase patterns at a first time, wherein the first phase pattern provides a first adjustment of the phase of the in-phase wavefront via at least a first phase adjustment amount of the first pixel and a second phase adjustment amount of the second pixel; and
generating a second phase pattern included in the different phase patterns at a second time, wherein the second phase pattern provides a second adjustment of the phase of the in-phase wavefront via at least a third phase adjustment amount of the first pixel and a fourth phase adjustment amount of the second pixel, and wherein the first adjustment of the phase is different than the second adjustment of the phase.

4. The near-to-eye display of claim 1, wherein the multiple pixels include electrowetting elements.

5. The near-to-eye display of claim 1, wherein the multiple pixels comprise liquid crystal cells.

6. The near-to-eye display of claim 1, wherein the near-to-eye display is a contact lens further comprising:
a transparent material having an eye-side opposite an external side, wherein the transparent material includes a biocompatible material suitable to be in contact with a human eye, and wherein the eye-side is curved to fit the human eye;
a substrate material, wherein the light source or the control logic is coupled to or disposed within the substrate material.

7. The near-to-eye display of claim 1, wherein the optical system includes:
a waveguide positioned to receive the illumination light from the light source; and
an outcoupling optical element configured to outcouple the illumination light from the waveguide to the phase map as the in-phase wavefront.

8. The near-to-eye display of claim 7, wherein the control logic is adapted to provide signals to the phase map via one or more signal lines disposed on the waveguide.

9. The near-to-eye display of claim 1, wherein the optical system further includes:
a collimating element disposed between a waveguide and the light source, wherein the collimating element collimates the illumination light; and
a receiving optical element configured to direct the illumination light through the waveguide, wherein the receiving optical element receives the illumination light after the illumination light propagates through the collimating element.

10. The near-to-eye display of claim 9, wherein the receiving optical element includes a reflective Bragg grating to direct the illumination light through the waveguide.

11. The near-to-eye display of claim 1, wherein the phase map includes an array of transparent pixels and wherein each transparent pixel is to advance or retard a photon of the respective portions of the in-phase wavefront according to the different phase patterns.

12. The near-to-eye display of claim 1, wherein the phase adjustment amount of each of the multiple pixels is based on discrete level.

13. The near-to-eye display of claim 12, wherein the control logic is coupled to the phase map to perform further operations including:
varying a transmitted amplitude of a photon of the respective portion of the in-phase wavefront based on a transparency value of each of the multiple pixels.

14. The near-to-eye display of claim 1, wherein each of the multiple pixels advance or retard a photon of the respective portion of the in-phase wavefront according to the different phase patterns, and wherein the control logic is coupled to the phase map to perform further operations including:
varying a transmitted amplitude of the photon of the respective portion of the in-phase wavefront based on a transparency value of each of the multiple pixels.

15. The near-to-eye display of claim 1, wherein the control logic is configured to dynamically change the phase adjustment amount of the multiple pixels at different times to generate the different phase patterns to form the respective image at the different times.

16. The near-to-eye display of claim 1, wherein the illumination light includes different respective wavelengths, wherein the light source is configured to sequentially emit the different respective wavelengths of the illumination light, and wherein the control logic is configured to generate control signals to successively illuminate a first phase pattern, included in the different phase patterns, with the different respective wavelengths.

17. A system comprising:
a smart contact lens comprising:
a light source to emit illumination light;
an optical system configured to receive the illumination light from the light source and output the illumination light as an in-phase wavefront; and
a phase map including multiple pixels each positioned to receive a respective portion of the in-phase wavefront, wherein the multiple pixels are configured to collectively spatially modulate a phase of the in-phase wavefront; and
control logic including circuitry coupled to the phase map to generate different phase patterns with the phase map by configuring a phase adjustment amount of the multiple pixels, each of the different phase patterns to form a respective image at a retina-distance from the phase map as the in-phase wavefront propagates through the phase map in response to being illuminated by the in-phase wavefront; and
a base station communicatively coupled to the smart contact lens, wherein the base station is configured to wirelessly transmit communication data to the smart contact lens; and
wherein each of the different phase patterns are generated by the control logic in response to the smart contact lens receiving the communication data from the base station.

18. The system of claim 17, wherein the phase adjustment amount of each of the multiple pixels is independently configurable, and wherein the control logic is adapted to independently configure the phase adjustment amount of each of the multiple pixels.

19. The system of claim 17, wherein the multiple pixels of the phase map includes a first pixel and a second pixel, and wherein the control logic is coupled to the phase map to perform operations including:
generating a first phase pattern included in the different phase patterns at a first time, wherein the first phase pattern provides a first adjustment of the phase of the in-phase wavefront via at least a first phase adjustment amount of the first pixel and a second phase adjustment amount of second pixel; and generating a second phase pattern included in the different phase patterns at a second time, wherein the second phase pattern provides a second adjustment of the phase of the in-phase wavefront via at least a third phase adjustment amount of the first pixel and a fourth phase adjustment amount of the second pixel, and wherein the first adjustment of the phase is different than the second adjustment of the phase.

20. The system of claim 17, wherein the phase map includes an array of transparent pixels and wherein each transparent pixel is configured to advance or retard a photon of the respective portions of the in-phase wavefront according to the different phase patterns.

21. The system of claim 17, wherein the phase adjustment amount of each of the multiple pixels is based on discrete levels.

22. The system of claim 17, wherein each of the multiple pixels is configured to advance or retard a photon of the respective portion of the in-phase wavefront according to the different phase patterns, and wherein the control logic is coupled to the phase map to perform further operations including:

varying a transmitted amplitude of the photon of the respective portion of the in-phase wavefront based on a transparency value of each of the multiple pixels.

* * * * *